(12) United States Patent
Floyd et al.

(10) Patent No.: US 10,551,162 B2
(45) Date of Patent: Feb. 4, 2020

(54) CODE-MODULATED PHASED-ARRAY INTERFEROMETRIC IMAGING

(71) Applicant: North Carolina State University, Raleigh, NC (US)

(72) Inventors: Brian Floyd, Raleigh, NC (US); Vikas Chauhan, Raleigh, NC (US); Kevin Greene, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 57 days.

(21) Appl. No.: 15/570,096

(22) PCT Filed: May 6, 2016

(86) PCT No.: PCT/US2016/031247
§ 371 (c)(1),
(2) Date: Oct. 27, 2017

(87) PCT Pub. No.: WO2016/179513
PCT Pub. Date: Nov. 10, 2016

(65) Prior Publication Data
US 2018/0149466 A1    May 31, 2018

Related U.S. Application Data

(60) Provisional application No. 62/157,658, filed on May 6, 2015.

(51) Int. Cl.
*G01B 9/02* (2006.01)
*G01S 13/90* (2006.01)
(Continued)

(52) U.S. Cl.
CPC ..... *G01B 9/02084* (2013.01); *G01B 9/02041* (2013.01); *G01K 11/006* (2013.01);
(Continued)

(58) Field of Classification Search
CPC .. G01B 9/02084; G01B 9/02041; H01Q 3/36; G01K 11/006; G01S 13/90; G01S 13/003; G01N 22/00
See application file for complete search history.

(56) References Cited

U.S. PATENT DOCUMENTS 6,868,201 B1 *  3/2005  Johnson .............. H04J 14/0209
                                                                    385/24
2004/0213351 A1  10/2004  Shattil
(Continued)

FOREIGN PATENT DOCUMENTS

EP    0831611 A2    3/1998

OTHER PUBLICATIONS

International Search Report for PCT/US2016/031247 dated Oct. 4, 2016.
(Continued)

*Primary Examiner* — Michael P LaPage
(74) *Attorney, Agent, or Firm* — Thomas | Horstemeyer, LLP; Christopher B. Linder; Jason M. Perilla

(57) ABSTRACT

Embodiments of a code modulated phased-array interferometer are described. In one embodiment, a code modulated phased-array interferometer includes a phased array having a plurality of receiver elements that receive a plurality of received signals. A code multiplexer multiplexes each of the plurality of received signals to generate a plurality of code multiplexed signals, and a combiner combines the plurality of code multiplexed signals into a combined signal. After other processing for signal reception, a code demultiplexer demultiplexes the combined baseband signal, and a complex correlator correlates unique pairs of baseband signals to generate a plurality of visibility products. Finally, the plurality of visibility products are transformed to generate an image. The concepts described herein may be relied upon to (Continued)

reconfigure or repurpose a phased-array receiver to achieve imaging.

20 Claims, 9 Drawing Sheets

(51) Int. Cl.
　　　G01K 11/00　　　(2006.01)
　　　H01Q 3/36　　　(2006.01)
　　　G01S 13/00　　　(2006.01)
　　　G01N 22/00　　　(2006.01)
(52) U.S. Cl.
　　　CPC ............... *G01S 13/90* (2013.01); *H01Q 3/36* (2013.01); *G01N 22/00* (2013.01); *G01S 13/003* (2013.01)

(56) References Cited

U.S. PATENT DOCUMENTS

| 2006/0132383 | A1 | 6/2006 | Gally et al. |
| 2006/0222078 | A1 | 10/2006 | Raveendran |
| 2012/0212795 | A1 | 8/2012 | Ganti et al. |
| 2012/0257197 | A1 | 10/2012 | Feldkhun et al. |
| 2014/0078298 | A1 | 3/2014 | Kudenov et al. |
| 2016/0056883 | A1* | 2/2016 | Fujimura ............... H04B 1/005 370/325 |

OTHER PUBLICATIONS

T. Wang (2003) "Observing Strategies at Millimetre Wavelengths" ATNF Narrabri Synthesis Workshop.
E Carpentieri; et al (2008) "Millimeter-Wave Phased-Array Antennas" IEEE Radar Conference, pp. 1-5.
RnRMarketResearch.com (2014) "45.09% CAGR for Millimeter Wave Technology Market Forecast for 2020, Says a New Industry Research Report Available With RnRMarketResearch.com" PRNewswire, pp. 1-27.
M. Rosker, (2007) "Engineering the ideal array," Microsystems Technology Symposium, pp. 1-17. http://www.mtosymposium.org/2007/proceedings.htm.
KJ. Koh; et al (2009) "A Millimeter-Wave (40-45 GHz) 16-Element Phased-Array Transmitter in 0.18-mm SiGe BiCMOS Technology" IEEE Journal of Solid-State Circuits, vol. 44, No. 5, pp. 1498-1509.
B. Floyd; et al., (2006) "A silicon 60GHz receiver and transmitter chipset for broadband communications," IEEE ISSCC Dig. Tech. Papers, pp. 184-185.
G. R. Huguenin, (1997) "Millimeter Wave Concealed Weapon Detection and Through-the-Wall Imaging Systems," Proc. SPIE, vol. 2938, pp. 152-159.
A. R. Harvey; et al (2000) "Prospects for mm-Wave Aperture Synthesis for Space-Borne and Aerial Platforms," Proc. SPIE, vol. 4091, pp. 27-38.
R. Appleby, et al., (2004) "The Design of a Real Time 94GHz Passive Millimeter Wave Imager for Helicopter Operations," Proc SPIE, vol. 5619, pp. 38-46.
H. P. Moyer, et al., (2007) "A Low Noise Chipset for Passive Millimeter-Wave Imaging," Proc. Int. Microwave Symp., pp. 1363-1366.
P. F. Goldsmith, et al (1993) "Focal Plane Imaging Systems for Millimeter Waves," IEEE Trans. Microwave & Tech., vol. 41, No. 10, pp. 1664-1675.
J. Powell; et al (2008) "SiGe Receiver Front Ends for Millimeter-Wave Passive Imaging," IEEE Trans. Microwave & Tech., vol. 56, No. 11, pp. 2416-2425.
J. W. May; et al (2009) "High-Performance W-Band SiGe RFICs for Passive Millimeter-Wave Imaging," IEEE RFIC Symp. Dig. Papers, pp. 437-440.
S. K. Reynolds; et al (2010) "A 16-Element Phased-Array Receiver IC for 60-GHz Communications in SiGe BiCMOS," IEEE RFIC Symp. Dig. Papers, pp. 461-464.
A. Valdes-Garcia; et al (2010) "A SiGe BiCMOS 16-Element Phased-Array Transmitter for 60GHz Communications," IEEE ISSCC Dig. Tech. Papers pp. 218-220.
M. Ryle; et al (1959) "The Synthesis of Large Radio Telescopes by the Use of Radio Interferometers," IEEE Trans. Ant. & Prop., pp. S120-S124.
D. M. Le Vine (1999) "Synthetic Aperture Radiometer Systems," IEEE Trans. Microwave Theory & Tech., vol. 47, No. 12, pp. 2228-2236.
B. Lambrigtsen; et al (2004) "GeoSTAR—a Synthetic Aperture Approach for a Geostationary Microwave Sounder," Proc. IEEE Aerospace, vol. 2, pp. 1008-1014.
A. Pergande (2007) "New Steps for Passive Millimeter Imaging," Proc. SPIE, vol. 6548, pp. 654802-1-654802-4.
P. Kangaslahti, et al., (2008) "Millimeter-Wave Synthetic Thinned Aperture Radiometer," 2008 Int. Conf. Infrared, Millimeter and Terahertz Waves, pp. 1-2.
A. B. Tanner; et al (1993) "Calibration of a Synthetic Aperture Radiometer," IEEE Trans. Geoscience and Remote Sensing, vol. 31, No. 1, pp. 257-267.
F. Torres; et al (1996) "On-Board Phase and Modulus Calibration of Large Aperture Synthesis Radiometers: Study Applied to MIRAS," IEEE Trans. Geosci. Rem. Sen., vol. 34, No. 4, pp. 1000-1009.
F. Tzeng; et al (2009) "A CMOS Code-Modulated Path-Sharing Multi-Antenna Receiver Front-End," IEEE J. Solid-State Circuits, vol. 44, No. 5, pp. 1321-1335.
M. Duarte; et al (2008) "Single-Pixel Imaging Via Compressive Sampling," IEEE Signal Processing Magazine, pp. 83-91.
J. Lynch; et al (2010) "Performance Limitations of Compressive Sensing for Millimeter Wave Imaging," Proceedings of the SPIE, vol. 7670, pp. 76700D-76700D-8.
A. Camps; et al (2008) "Angular and Radiometric Resolution of Y-Shaped Nonuniform Synthetic Aperture Radiometers for Earth Observation," IEEE Geoscience and Remote Sensing Letters, vol. 5, No. 4, pp. 793-795.
J. L. Walsh (1923) "A Closed Set of Normal Orthogonal Functions," Am. J. Math, vol. 45, pp. 5-24.
Handerson, K.W. (1964) "Some Notes on Walsh Function," IEEE Transactions on electronic computer, pp. 50-52.
R. Korber; et al(2008) "Imaging Millimeter Wave Radar with Phased Array Antenna" Advanced Microsystems for Automotive Applications.
A. R. Thomas; et al (2001) "Interferometry and Synthesis in Radio Astronomy" 2nd edition, J. Wiley and Sons.

* cited by examiner

CODE-MODULATED PHASED-ARRAY INTERFEROMETRIC IMAGING

CROSS-REFERENCE TO RELATED APPLICATIONS

This application claims the benefit of U.S. Provisional Application No. 62/157,658, filed May 6, 2015, the entire contents of which are hereby incorporated herein by reference.

GOVERNMENT LICENSE RIGHTS

This invention was made with government support under grant number N66001-11-1-4144 awarded by the Defense Advanced Research Projects Agency. The government has certain rights in the invention.

BACKGROUND

Millimeter-wave (mm-wave) energy can penetrate clothing, fog, clouds, and other obscurants. As such, mm-wave sensors can be used for important applications, such as concealed-object detection, surveillance from unmanned airborne vehicles (UAVs), and aircraft navigation and landing systems, among others. Additionally, mm-wave cameras can be used for biomedical applications such as through-bandage imaging of wounds, measurement of skin burns, and through-clothing measurement of skin temperature.

BRIEF DESCRIPTION OF THE DRAWINGS

For a more complete understanding of the embodiments described herein and the advantages thereof, reference is now made to the following description, in conjunction with the accompanying figures briefly described as follows.

Figure 1A:
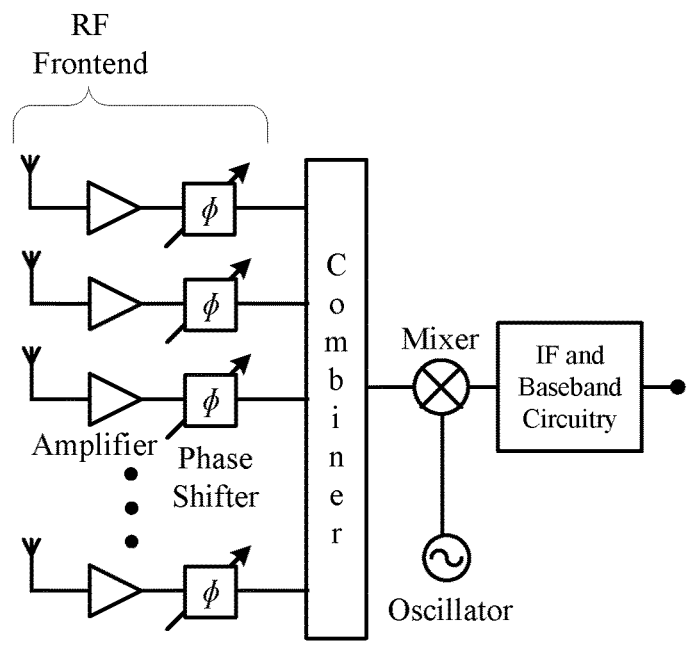
FIG. 1A illustrates an example block diagram of a phased-array receiver employing phase shifting and combining at the radio-frequency (RF) domain.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION

As noted above, mm-wave sensors can be used for important applications such as concealed-object detection, surveillance from UAVs, and aircraft navigation and landing systems, among other applications. Additionally, mm-wave sensors can be used for biomedical applications, such as through-bandage imaging of wounds, measurement of skin burns, and through-clothing measurement of skin temperature. Unfortunately, existing mm-wave sensors (e.g., cameras) are relatively large and heavy, due in part to the use of focusing lenses for a passive camera and low levels of integration achieved through using conventional III-V detectors for passive or active cameras.

Mm-wave focal-plane arrays (FPAs) are being explored as an option to measure mm-waves. However, FPAs may be bulky due to the use of lenses. Further, FPAs may be costly and difficult to manufacture, incorporating hundreds to thousands of individual antennas and detectors. According to aspects of the embodiments described herein, a more desirable solution for passive imaging is to leverage, at least in part, already-developed electronics in a new way to capture mm-wave images. Such a solution could allow for flat or conformal imaging arrays without requiring a lens, suitable for lightweight UAVs. The approach is applicable to commercial-off-the-shelf (COTS) 60- and 77-GHz phased arrays, although not limited to those frequencies or frequency ranges, resulting in low-cost sensors or cameras for security portals, navigation systems, and biomedical imagers, for example.

In the context described above, the embodiments described herein are related to architectures that reconfigure various phased array or beamformer receiver platforms as interferometric imaging systems. Using phased-array hardware platforms, such as those developed for communication or automotive radar applications, for example, lower cost imaging systems can be developed. In some cases, systems which contain phased array hardware (e.g., aircraft, ships, etc.) can use these arrays in a different mode to provide imaging capabilities. The approach detailed herein may be generally described as code-modulated interferometry. The approach can be used for both active and passive imaging scenarios, where either external or ambient illumination is used.

A phased array or beamformer receiver may include N antennas and receiver (Rx) chains, where each Rx chain includes a combination of amplifiers, filters, phase shifters, time shifters, downconverters, etc. While a phased-array receiver performs various operations related to filtering, amplifying, frequency converting, and other operations, another key operation of a phased array receiver is beamforming operations. As a non-limiting example, beamforming refers to a process where signals received by individual receiver elements are amplitude, phase, and/or time shifted and then combined together. Through adjusting of the amplitude, phase, and/or time shift within the array, a beam pattern response can be synthesized such that signals arriving at the receiver from a desired direction combine coherently and signals arriving at the receiver from an undesired direction combine destructively.

Figure 1B:
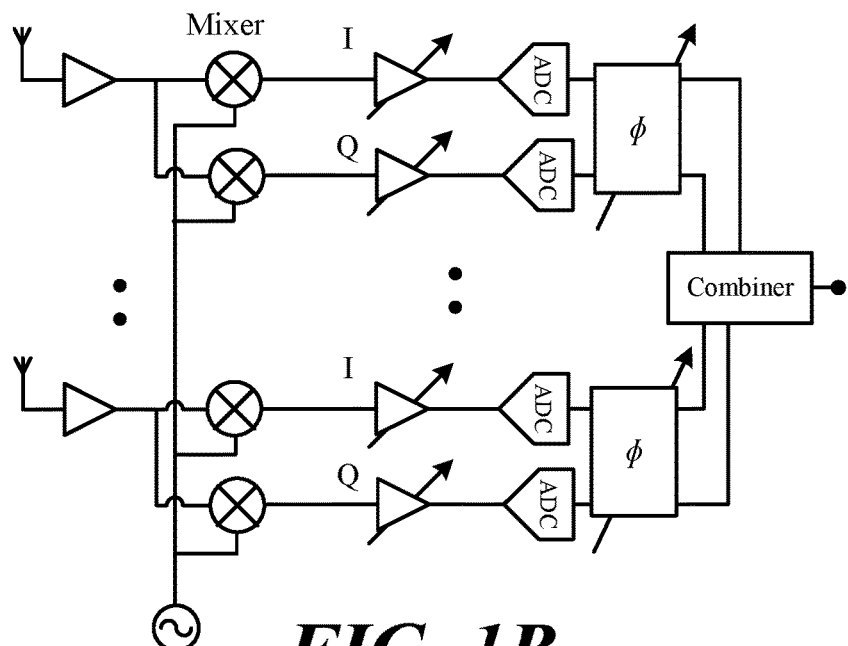
FIG. 1B illustrates an example block diagram of a phased-array receiver employing phase shifting and combining in the digital domain.

The architecture of phased array receivers may vary in a number of ways. FIG. 1A illustrates an example block diagram of a phased array receiver employing phase shifting and combining at the radio-frequency (RF) domain. Because it combines in the RF domain, the receiver in FIG. 1A shares a downconversion path (e.g., mixer, local oscillator, baseband amplifiers and filters, data converters, etc.) to save on hardware complexity and cost. An alternative approach is shown in FIG. 1B, which illustrates an example block diagram of a phased-array receiver employing phase shifting and combining in the digital domain. For the receiver shown in FIG. 1B, individual signals are phase shifted and combined after downconversion to a low frequency (i.e., baseband). In this approach, beamforming is performed in the digital domain. As can be seen, this approach provides great flexibility, although N parallel receive paths from RF to baseband are required, and the hardware overhead is large. Though not summarized here, alternative approaches to building a phased array receiver are known, such as those relying on phase shifting a local oscillator and combining after mixing, and these arrays can likewise be repurposed or reconfigured as imagers according to the concepts described herein.

According to aspects of the embodiments, the following three key concepts are leveraged to achieve imaging using a phased array receiver: interferometry, code modulation, and system integration. The first key concept is that passive imaging is realized through radio interferometry. Radio interferometry or synthetic-aperture radiometry is a technique used by radio astronomers to realize higher resolution telescopes using a sparse array of coherent detectors to sample an aperture. Interferometry does not require a focusing lens, allowing for "thinned" or conformal arrays. In the basic operation of interferometry, amplitude and phase data taken from uniquely-spaced pairs of detectors (referred to as "baselines") are interfered, forming fringe patterns related to the scene through an inverse Fourier transformation. An interferometer array, therefore, has to capture each independent information stream, generate pair-wise correlations, and then transform those correlations into an image.

Figure 1C:
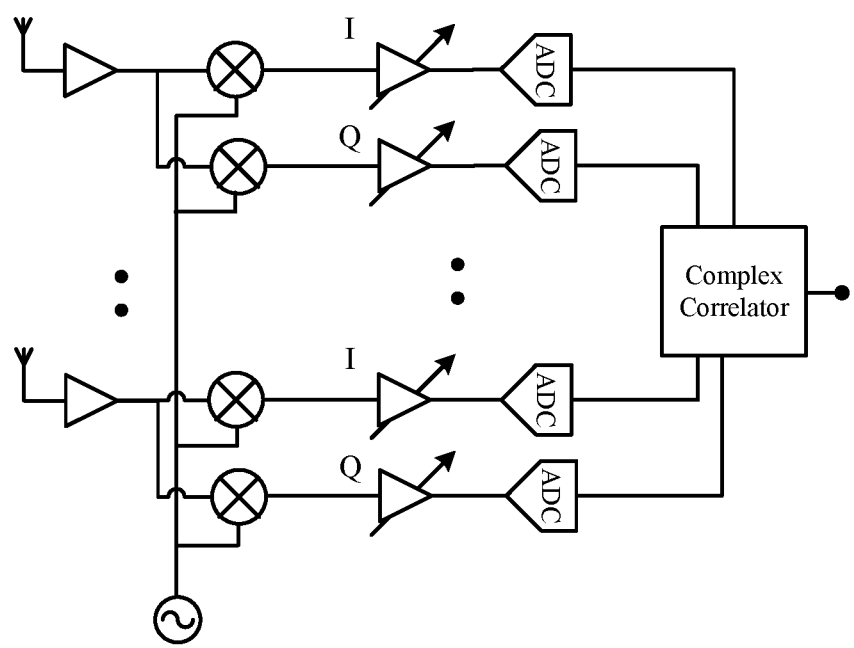
FIG. 1C illustrates an example block diagram of an interferometer array.

A traditional approach to realizing an interferometer array is shown in FIG. 1C, which resembles the beamforming receiver in FIG. 1B. As shown in FIG. 1C, the complex correlation between each baseband in-phase (I) and quadrature (Q) baseline signal is calculated. This architecture is quite different from the architecture of a traditional phased-array receiver (e.g., FIG. 1A). Specifically, an RF-combined phased-array receiver combines all signals directly at RF, meaning that it is no longer possible to recover the individual signals and/or the correlations between individual signals.

The second key concept is the incorporation or use of code modulation in phased-array receivers. Code modulation allows multiple, individual radiometer data streams to be multiplexed onto a single Rx chain. Using code modulation, baselines from each RF front end of a phased-array receiver are orthogonally modulated using existing receiver components (e.g., phase shifters, variable-gain amplifiers, etc.) to multiplex the baselines through the rest of the receiver. Within phase-array receivers, signal combinations generally occur during beamforming (i.e., as shown in FIG. 1A). In the code-modulated phased-array interferometer devices described herein, however, necessary information in the individual received baseline signals is retained. More specifically, it is possible to measure the complex cross-correlations between all of the individual baselines. Thus, to achieve interferometric measurements using a traditional phased array receiver, a multiple-access (e.g., code-division multiple access) technique is applied to share a single hardware chain while maintaining the information in the respective baselines.

Using code modulation, each individual data stream or baseline within each Rx chain of the phased array is tagged or multiplied by an orthogonal code (e.g., PN, Walsh, Gold, etc.) before they are combined. Code modulation essentially turns the beamforming operation of a phased array receiver into a code-multiplexing operation. This orthogonal code modulation can occur using the phase shifters in the front end of a phased-array receiver, for example. The multiplexed channels are then processed through a single downconversion and sampling operation, retaining coherency.

Once in the digital domain, the data is code demultiplexed so that complex correlations between received antenna signals can be obtained. The complex correlations or visibility functions are, in turn, used for image reconstruction using interferometric techniques. As will be discussed is further detail below, there are multiple approaches to the code demodulation process. For example, individual complex-valued signals can be first demultiplexed and then complex correlated, or the complex correlations can be themselves code demodulated.

The third key concept is leveraging a highly-integrated mm-wave phased array platform with embedded data processing. As orthogonal code modulation is performed within a phased-array receiver and demodulation is performed at a later point within the system, coherency becomes important to retain orthogonality. Systems which have embedded digital processing become attractive for this reason. For example, silicon-based phased arrays are becoming more prevalent, particularly for emerging applications such as 60-GHz wireless communication systems and 77-GHz vehicular radar systems. These silicon-based arrays provide embedded modulation, demodulation, multiplexing, and demultiplexing processes using a small number of integrated circuits. In turn, this eases the coherency requirements within the system. Although high levels of integration are beneficial, they are not absolutely necessary to reduce the concepts described herein to practice. It is also possible to reconfigure or repurpose a discrete phased-array receiver into an interferometric imaging system according to the concepts described herein. Additionally, it is also possible to control a phased-array receiver through a digital interface and eliminate the need to include on chip modulators.

One benefit of the concepts described herein is the realization of an interferometer array for imaging with less hardware. Specifically, N uniquely-spaced detectors or baselines result in N(N−1)/2 correlation products to be measured, meaning that fewer mm-wave detectors can be used to obtain an image at the cost of more digital computations. For example, 16 to 64 elements can sample 120 to 2016 baselines, respectively. One key aim of an interferometer array is coherency between the detectors, as both amplitude and phase relationships at the antenna should be retained down to baseband. It is noted that the reconfigured or repurposed phased-array receivers described herein are not used to simply focus a beam and then scan that beam over the field-of-view (FOV). Instead, "snapshot" imaging is obtained through taking interferometric measurements of the entire FOV using the full available frame period.

Figure 2:
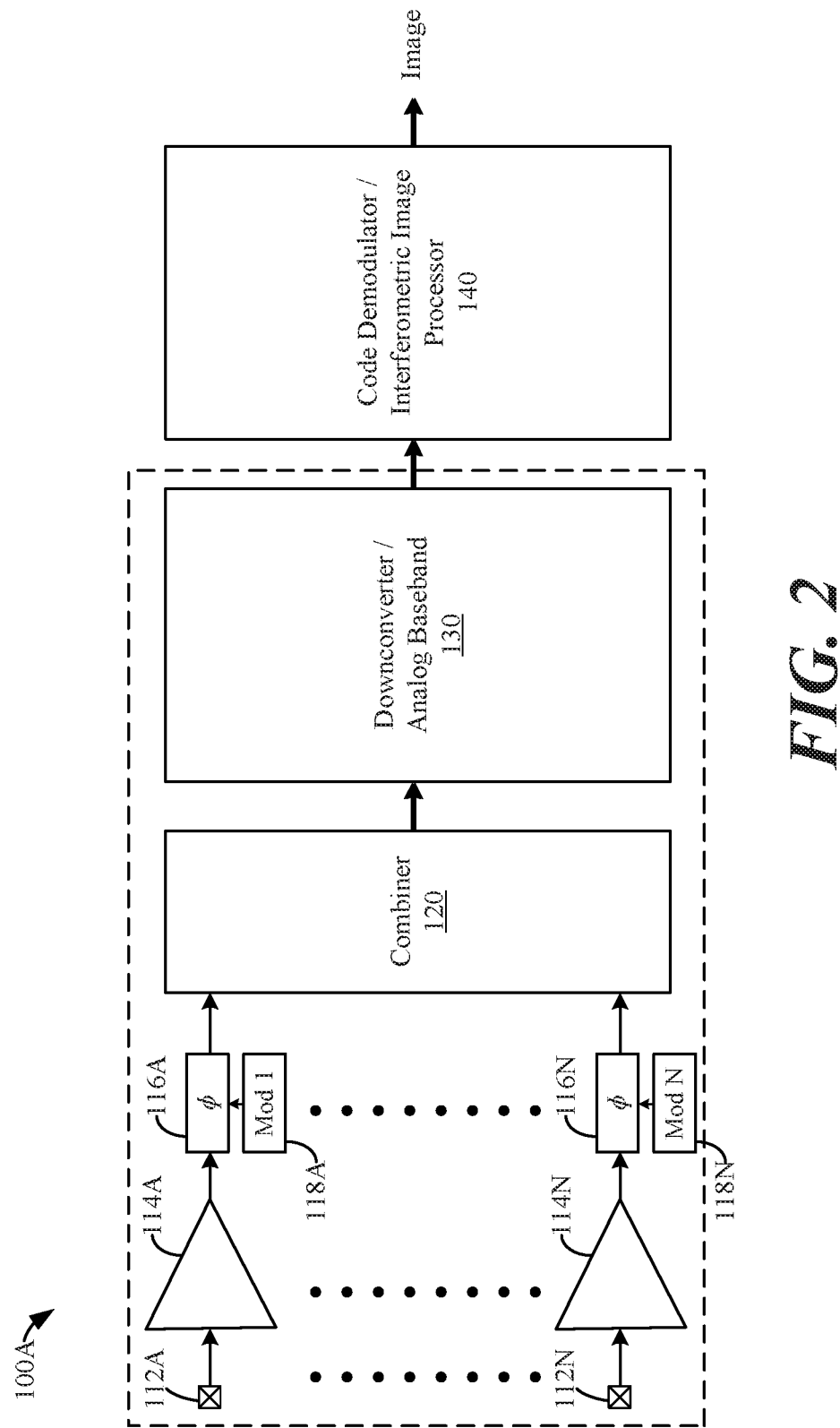
FIG. 2 illustrates a code-modulated phased-array interferometer according to one example embodiment described herein.

Turning to the remaining drawings, various embodiments of code-modulated phased-array interferometers are described in further detail. FIG. 2 illustrates a code-modulated phased-array interferometer 100A ("interferometer 100A") according to one example embodiment described herein. The interferometer 100A in FIG. 2 is provided by way of example and is not intended to be limiting as to the scope of the embodiments or the possible variations thereof.

Among other elements, the interferometer 100A includes antenna elements 112A-112N ("antenna elements 112"), amplifiers 114A-114N ("amplifiers 114"), phase shifters 116A-116N ("phase shifters 116"), orthogonal code source modulators 118A-118N ("code modulators 118"), a combiner 120, a downconverter 130, and a code demodulator/interferometric image processor 140 ("image processor 140"). In the interferometer 100A, individual signals or baselines, such as the baseline captured at the antenna element 112A, are phase shifted and combined in the RF domain. Because the combined signals share the same downconversion path (e.g., mixers, local oscillators, baseband amplifiers and filters, analog to digital converters, etc.) in the downconverter 130, the interferometer 100A saves on hardware complexity and cost.

The antenna elements 112 may include N elements selected to take interferometric measurements from an existing M-element phased-array receiver. The locations of such N antenna elements can be selected to give a preferred spatial coverage for aperture synthesis. For example, "X," "Y," or "T" shaped crosses can be used as described below with reference to FIG. 5A, and are common because they provide good spatial coverage and angular resolution. Signals received on the antenna elements 112 are amplified and/or filtered by the amplifiers 114, and the phase shifters 116 code multiplex each of the received signals, respectively, using unique codes generated by the modulators 118. Thus, the phase shifters 116 output a plurality of code-multiplexed signals.

In the interferometer 100A, the rate of code modulation is related to the rate of change within the scene being imaged and/or the length of the codes being used, and is not related to the (carrier) frequency of the incoming received signals. Put another way, the incoming received signals will have amplitude and phase fluctuations related to how the scene is changing. The orthogonal modulation should therefore be much faster than these scene changes. If scenes change slowly, the modulation rate can be slow as well. As a result, there is very little spectrum "spreading" through this modulation process, meaning that the receiver bandwidth does not need to be increased to accommodate such signals. This is a significant difference as compared to CDMA for wireless communications, where the "chip rate" has to be much larger than the symbol rate, resulting in significant signal spreading. Thus, in the embodiments described herein, the code-set for code modulation can have a chip rate selected based on the rate of scene change in captured images rather than the symbol rate for data communications.

After code modulation, the combiner 120 combines the N code-multiplexed signals from the phase shifters 116 into a combined signal, and the combined signal is processed through the rest of the Rx chain in the downconverter 130. The downconverter 130 downconverts the combined signal to a baseband or lower-frequency (e.g., intermediate frequency) combined signal. The downconverter 130 can also convert (e.g., analog to digital convert) the combined baseband signal for further processing in the digital domain. In the digital domain, the combined signal is code demultiplexed by the image processor 140. That is, the image processor 140 performs an inverse of the code modulation process in the digital domain to decode N baseband signals from the combined baseband signal. After being code demultiplexed in the digital domain, the image processor 140 correlates unique pairs of the N baseband signals to generate a plurality of visibility functions. These complex correlations or "visibility functions" are used for interferometry imaging.

In interferometry, complex correlations between signals must be measured. These correlations are often termed visibility functions. In a generalized receiver system, complex signals are broken down into I and Q components. For interferometry, the complex correlation or visibility refers to the correlation between Ij and Ik (the real visibility) as well as the correlation between Ij and Qk. (the imaginary visibility). The correlation between Qj and Qk is another measure of the real visibility and the correlation between Qj and Ik is another measure of the imaginary visibility. These measurements can be used as additional redundant data points. The complex correlations can be measured for all signal (or antenna) pairs of interest.

In some embodiments, code modulation is applied to both I and Q signals. One way this can be realized is through splitting the incoming received signals into I and Q components and then code modulating each component with a respective, unique code. Such an operation, for example, could be directly realized using a type of phase shifter known as a vector interpolator. As will be shown, however, any phase shifter topology can be used provided that it can shift the phase by at least 90 degrees. Mathematically, I and Q phase modulation can be represented through the multiplication of the input signal by a complex code $c_n = i_n + jq_n$, where j represents the imaginary number (square root of negative one), $i_n$ represents the code applied to the I component of the signal, and $q_n$ represents the code applied to the Q component of the signal. Through such a complex modulation, it is possible to retrieve both the in-phase and quadrature-phase portions of an incoming signal which can then be used for complex correlation measurements.

Such complex code modulation can be realized in a two-bit phase shifter, i.e., one that can shift the phase by a least significant bit of 90 degrees. Many phased arrays include at least two-bit phase shifters. Thus, these phase shifters can be used to impart complex code modulation. Even if the received signals are not split into I and Q signals, a two-bit phase shifter can provide such complex modulation.

The operation of a phase-shifter-based orthogonal modulation can be described mathematically. Assume that the input signal for element n is given by:

$$s_n(t) = A_n \cos(\omega_o t + \theta_n) \quad (1)$$

where $A_n$ and $\theta_n$ are the amplitude and phase of the $n^{th}$ signal and $\omega_o$ is the center frequency of the signals of interest arriving at the receiver. Each signal received within the phased array will eventually undergo either a time or phase shift in addition to a potential amplitude scaling. Here, the scenario of phase shifting is discussed, although the approach should not be considered to be limited to only phase shifting. Additionally, it can be assumed that the frequency-dependent response of each element, e.g., the frequency response of an amplifier, filter, phase shifter, etc., can be subsumed within gain and phase factors $A_n$ and $\theta_n$. If element n imparts a phase shift of $\phi_n$, where for two-bit phase shifting $\phi_n$ takes values of either ±45° or ±135°, then the phase-shifted signal at the output of the array element can be represented as:

$$s_n'(t) = A_n' \cos(\omega_o t + \theta_n' - \phi_n). \quad (2)$$

This signal can be rewritten as a summation of I and Q signal components using simple trigonometry, as follows:

$$\begin{aligned}s_n'(t) &= A_n' \cos(\phi_n)\cos(\omega_o t + \theta_n') + A_n' \sin(\phi_n)\sin(\omega_o t + \theta_n') \\ &= i_n\left[A_n'\frac{\sqrt{2}}{2}\cos(\omega_o t + \theta_n')\right] + q_n\left[A_n'\frac{\sqrt{2}}{2}\sin(\omega_o t + \theta_n')\right] \\ &= i_n s_{i1} + q_n s_{q1},\end{aligned} \quad (3)$$

where $i_n$ and $q_n$ represent balanced orthogonal codes having values of either +1 or −1 used to multiplex the I and Q components of the signal, respectively. Thus, a two-bit phase shifter can be used to impart independent code modulations to both the in-phase and quadrature-phase components of the incoming signal. Correlating the phase-shifted signal s'(t) with $i_n$ will result in the I component of the signal, $s_{in}$, and correlating the phase-shifted signal s'(t) with $q_n$ will result in the Q component of the signal, $s_{qn}$.

Figure 3:
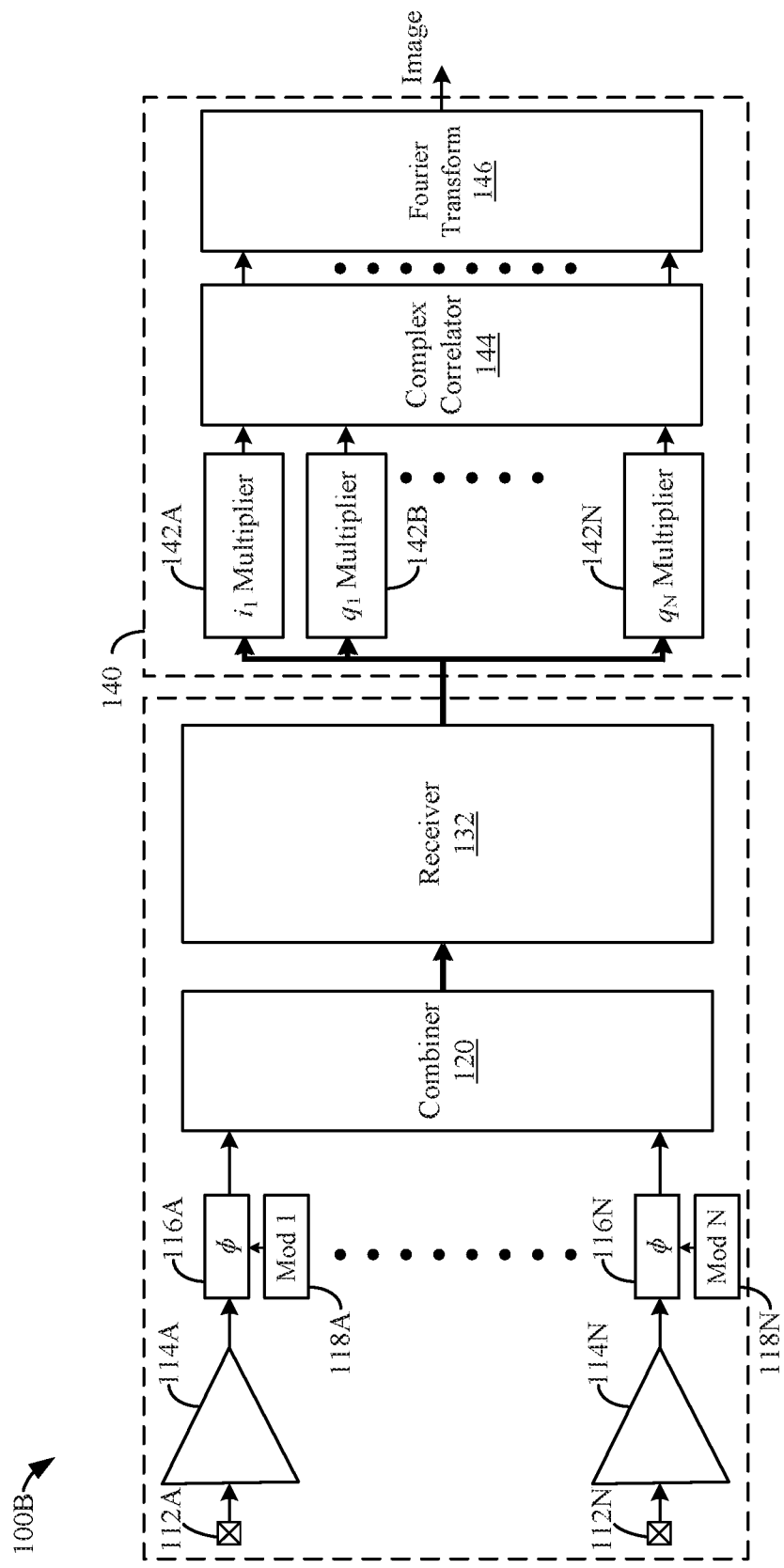
FIG. 3 illustrates another code-modulated phased-array interferometer according to another example embodiment described herein.

A complex correlation performed by the image processor 140 in FIG. 2 refers to a process where the complex correlations or visibility functions between each pair of incoming signals are recovered. Because the incoming signals have been orthogonally multiplexed using complex codes and then combined, the process includes both demultiplexing and complex correlation. One approach to the demultiplexing and complex correlation processes is shown in FIG. 3. FIG. 3 illustrates another code-modulated phased-array interferometer 100B according to one example embodiment described herein. In the interferometer 100B, the image processor 140 includes code multipliers or demultiplexers 142A-N ("demultiplexers 142"), a complex correlator 144, and a Fourier Transformer 146.

As was the case in FIG. 2, each incoming received signal in FIG. 3 is multiplexed using a complex code at the front-end phase shifter. The signals are then combined at the combiner 120. Depending upon the structure of the receiver 132, which may be similar or different in form and/or structure as compared to the downconverter 130 in FIG. 2, the combined signal can either be an analog signal at radio frequency, an analog signal at intermediate frequency, an analog signal at baseband frequency, or a digital signal at baseband frequency. The combined signal can be expressed as:

$$s_{sum} = \sum_n k_n(i_n s_{I,n} + q_n s_{Q,n}) \approx k_c \sum_n (i_n s_{I,n} + q_n s_{Q,n}), \quad (4)$$

where, $s_{I,n}$ and $s_{Q,n}$ represent the I and Q components of the $n^{th}$ signal, respectively. These are time-varying signals, where the time notation has been dropped (i.e., $s_{sum}(t) \rightarrow s_{sum}$). The combiner 120 may potentially introduce frequency-dependent gain and phase terms, represented by $k_n$. For well-designed combiners, such gain and phase responses are generally the same (or having known offsets) for each element and can therefore be placed outside the summation, represented by $k_c$. For the remaining derivations, it can be assumed that $k_n$ can be measured and compensated as needed using known techniques to observe gain and phase offsets between elements. Additionally, "normalized summations" can be used, where $k_c$ is allowed to be one, where $k_c$ essentially becomes a scalar applied to all visibilities.

After being output from the receiver 132, the combined signal is first demultiplexed using a "half-demultiplexer" stage at the demultiplexers 142. The demultiplexers 142 multiply or demultiplex the combined signal with the individual codes ($i_1$, $q_1$, $i_2$, $q_2$, $i_3$, $q_3$, . . . , $i_N$, $q_N$). This operation is referred to as a half-demultiplexing since it is not immediately followed by integration by an integrator. These half-demultiplexed in-phase and quadrature-phase signals corresponding to I and Q signals can be expressed as follows:

$$\begin{aligned}s_{I,n}' &= i_n \cdot s_{sum} = s_{I,n} + i_n q_n s_{Q,n} + \sum_{m \neq n}(i_n i_m s_{I,m} + i_n q_m s_{Q,n}) \\ s_{Q,n}' &= q_n \cdot s_{sum} = s_{Q,n} + i_n q_n s_{I,n} + \sum_{m \neq n}(q_n i_m s_{I,m} + q_n q_m s_{Q,n})\end{aligned} \quad (5)$$

Note that these half-demultiplexed signals contain both the desired in-phase signal as well as all of the cross-products between independent codes. In a traditional CDMA demultiplexer or full demultiplexer, this multiplication would be followed by integration such that all portions related to the orthogonal codes are removed (e.g., only left with the average value of $s_{I,n}$ and $s_{Q,n}$). According to the concepts described herein, however, the integration step is omitted since imaging signals are in general zero mean and noise-like. As such, an integration would result in an average value of zero.

Interferometry relies on the complex correlations between incoming signal pairs. Thus, the multiplication step is immediately followed by a pairwise complex correlation step, where two half-demultiplexed signals of interest are cross-correlated. That is, they are multiplied together and then averaged over a sufficiently long time. These cross-correlation products are referred to as visibilities for interferometers. The complex visibilities are then represented as:

$$\begin{aligned}v_{Re,n,m} &= E(s_{I,n}' \cdot s_{I,m}') = E(i_n s_{sum} \cdot i_m s_{sum}) = E(i_n i_m s_{sum}^2) \\ &= 2 s_{I,n} s_{I,m} \\ v_{Im,n,m} &= E(s_{I,n}' \cdot s_{Q,m}') = E(i_n s_{sum} \cdot q_m s_{sum}) = E(i_n q_m s_{sum}^2) \\ &= 2 s_{I,n} s_{Q,m},\end{aligned} \quad (6)$$

where the $E(\cdot)$ notation is used to denote the expectation or integration function. In the derivations above, noise has not been included and there will be a component to these visibilities which relates to the average noise values within the system. Additionally, codes have been assumed to be perfectly orthogonal. However, code skew can result in partial correlation between codes and there will be "residues" remaining within the demodulated visibilities.

From equation (6), the operation of half-demultiplexing the signals and then performing a cross correlation is equivalent to correlating the square of the summation signal with a code product. This gives rise to a property of the code set to allow for correct demodulation. Since correlating the square of the summation with a code product, all code products should be balanced and orthogonal. This property is described as Balanced Orthogonal Code Products (BOCPs). In general, it is possible to have identical code products occur within a set of balanced orthogonal codes. This would result in multiple visibility functions obtained at once or conflicting one with the other. To avoid this, each code product should be balanced and orthogonal.

While the use of BOCPs can be used in general to avoid multiple visibility functions from conflicting one with the other, it is possible to use code sets which have redundant code products for use in the demodulation of redundant visibility functions. For example, pairs of antennas which have the same orientations and distances but are located in different parts of the array can be used to sample the same baselines. This, in turn, can be used to improve the sensitivity in the interferometer. Code modulation with code-sets having redundant code products can therefore be used for these redundant baselines.

Figure 4:
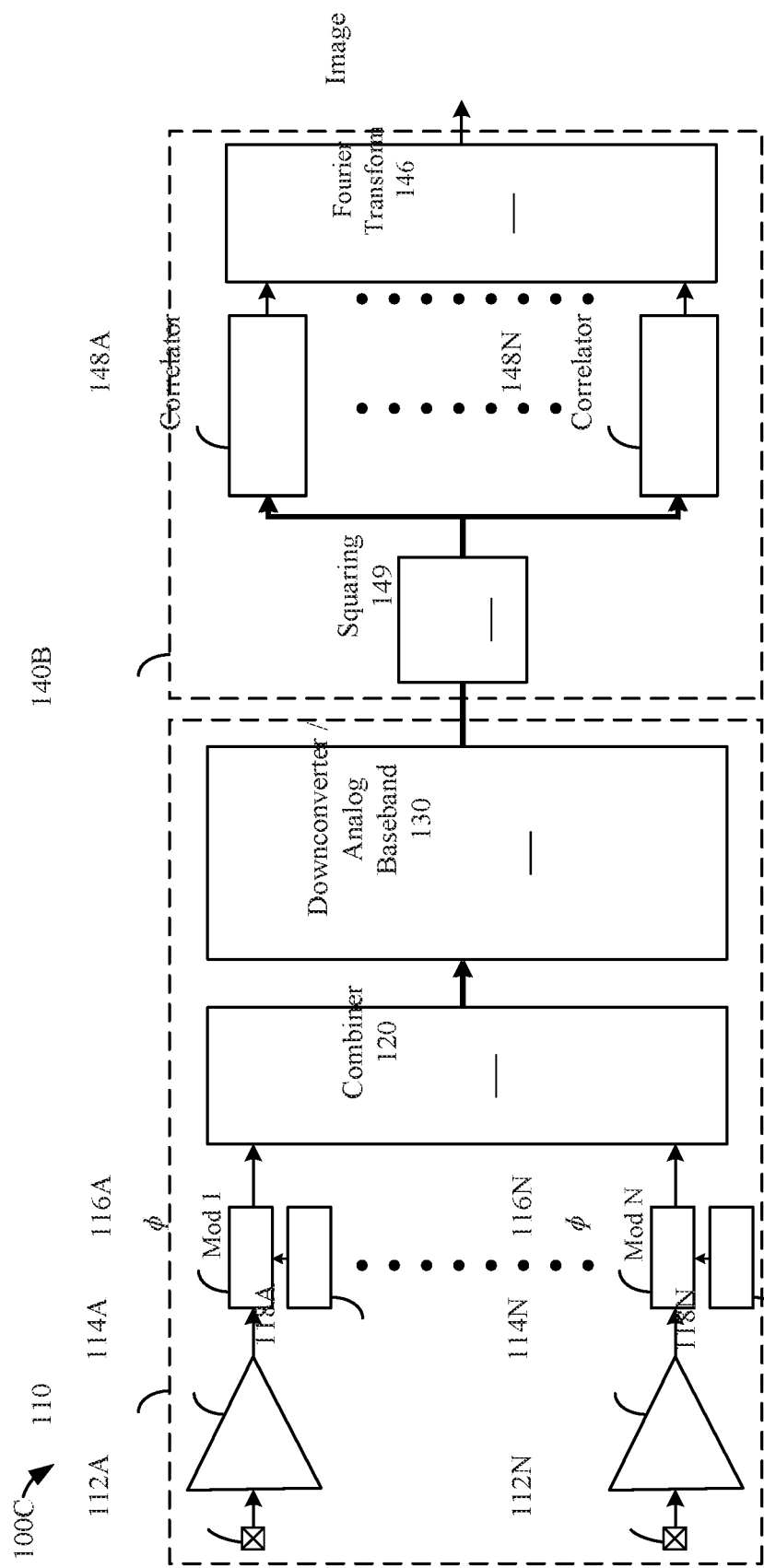
FIG. 4 illustrates another code-modulated phased-array interferometer according to another example embodiment described herein.

From equation (6), it is recognized that the demodulation process can be simplified to correlating a code product with the squared summation signal. Thus, a second approach to demodulation can be realized by a direct operation, as shown in FIG. 4. FIG. 4 illustrates another code-modulated phased-array interferometer 100C according to one example embodiment described herein. In the interferometer 100C, the image processor 140B includes a squaring block 149, correlators 148A-N ("correlators 148"), and the Fourier Transformer 146. Here, as before, each element is orthogonally modulated to create a combined complex code multiplexed signal $s_{sum}$. The downconverter and analog baseband 130 is optional and can be omitted for some embodiments, where the combined signal is directly coupled to the squaring block 149. For demultiplexing and demodulation, a signal "squaring" operation is applied at the squaring block 149. Such an operation can be an actual squaring circuit, such as a power detector, mixer, digital squaring operation, or another operation which creates an "interference" of the code-multiplexed signal with itself. The rationale for such a squaring operation is as follows. In a conventional interferometer, the two signals of interest are correlated or interfered to obtain the visibility products. In FIG. 4, the aggregate code-multiplexed signal is interfered with itself to obtain all possible visibility products, with the added result that these visibility products are now code modulated. The squared "power" signal p is represented as:

$$p = [s_{sum}]^2 = \sum_n |s'_n|^2 + 2\sum_n i_n q_n s_{I,n} s_{Q,n} + \qquad (7)$$
$$2\sum_{n \neq m}(i_n i_m s_{I,n} s_{I,m} + q_n q_m s_{Q,n} s_{Q,m} + i_n q_m s_{I,n} s_{Q,m}).$$

The squared summation or power signal p includes a summation of all of the "self-powers" of the individual signals, a summation of the in-phase and quadrature-phase cross-products of individual signals which are in general orthogonal to one another and would average to zero, and a summation of all of the code-modulated cross-products between signal pairs. This power signal is then correlated with code products $i_n i_m$ and/or $q_n q_m$ to obtain the real visibility samples. Likewise, the power signal is correlated with code products $i_n q_m$ to obtain the imaginary visibility samples, resulting in the following visibilities:

$$v_{Re,n,m} = E(i_n i_m \cdot p) = 2\overline{s_{I,n} s_{I,m}}$$
$$v_{Im,n,m} = E(i_n q_m \cdot p) = 2\overline{s_{I,n} s_{Q,m}}. \qquad (8)$$

This second stage can be interpreted as a demultiplexing operation applied to the signal cross-products. Again, in this approach, the code structure and properties should be carefully selected such that each code product is balanced and orthogonal to other code products. Thus, a BOCP code-set can be used. In the interferometer 100C, it is possible to directly demodulate the visibilities without having to first half-demultiplex the individual signals and then cross-correlate them to obtain visibilities. As such, this approach presents an efficient way to obtain visibility information from code-modulated signals, as fewer multiplication and correlation steps are required.

Finally, it is important to point out that a given code-modulated array may employ "sub-arrays" of fewer elements, each element being code modulated, and each sub-array having its own demodulator block. As such, it is possible that a given system can employ either or both demodulator architectures.

One aspect of the code-modulated interferometry concepts described herein makes use of a code-set which has BOCPs. To help evaluate and identify BOCP code-sets, different techniques can be used, including Rademacher codes, whose products can be shown to result in Walsh code sets. One aspect of BOCPs is that longer code-sets are in general needed, as different codes can have the same code products. For example, for a Walsh code of length eight, only four codes can be used to result in BOCPs. One allowable group of four is $W_2$, $W_3$, $W_4$, and $W_5$. Use of these codes for modulation results in the following possible code products from the same set: $W_2$, $W_3$, $W_4$, $W_6$, $W_7$, and $W_8$. $W_1$ is not used as it is all ones. Codes $W_6$, $W_7$, and $W_8$ are not used for modulation since they result in repeated code products.

The code-modulated phased-array interferometer embodiments described herein can be used with either ambient (i.e., passive) or active illumination. Passive imaging relies on ambient illumination which occurs at mm-wave frequencies (e.g., from cold sky). This ambient radiation is blackbody in nature, with power level proportional to the temperature of the source. Outdoors, cold sky appears as 100K source, people and surroundings appear as 300K source, providing a contrast ratio of 200K. Indoors, the subject and surroundings are at similar temperatures and the contrast ratio is only around 10-15K. As such, very sensitive receivers are required to detect small temperature differences. Active imaging relies upon illumination to elevate the signals above the noise floor. Illumination can be at a single frequency, akin to a radar, or a wide range of frequencies, akin to a "white light" flashbulb. Illumination may be provided in various ways, such as using COTS mm-wave transmitters to provide broadband illumination on the target. These can be modulated with pseudo-random Gigabit-per-second codes to provide broadband "white" illumination. Fluorescent light bulbs can also be used to provide mm-wave illumination.

Figure 5A:
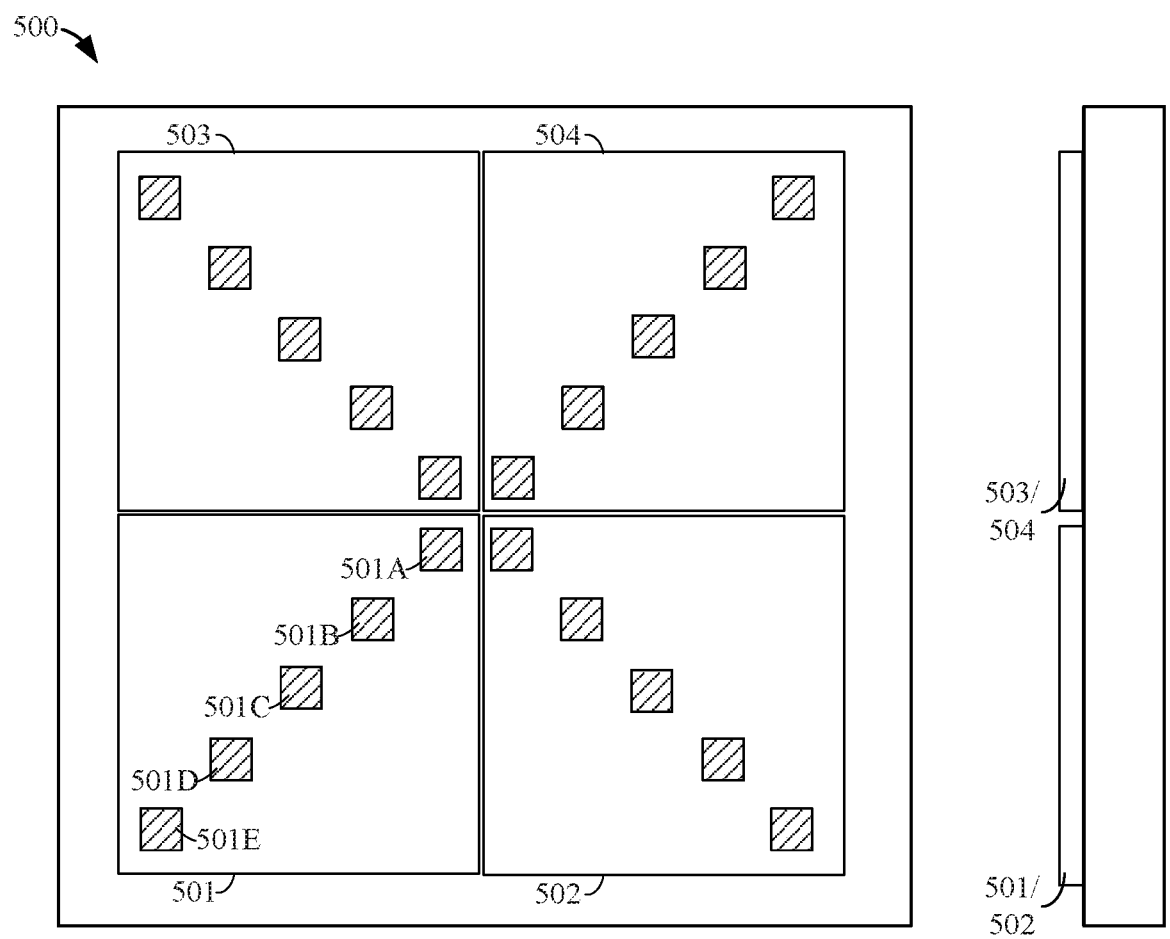
FIG. 5A illustrates an example antenna array for use with one or more of the interferometers in FIGS. 2-4, according to various embodiments described herein.

FIG. 5A illustrates top-down and side views of an example antenna array 500 for use with one or more of the interferometers in FIGS. 2-4. In FIG. 5A, the antenna 500 includes an arrangement of antenna elements or facets (e.g., similar to the antenna elements 112 shown in FIGS. 2-4) distributed along an outside surface of phased-array circuit packages 501-504. As shown, the phased-array circuit package 501 includes antenna elements 501A-501D, and the phased-array circuit packages 502-504 include similar antenna elements 501A-501D. Together, the phased-array circuit packages 501-504 can be mounted on a printed circuit board to provide N antenna elements to take interferometric measurements. In various embodiments, any suitable number of antenna elements can be included per phased-array antenna package, such as 4, 8, 16, or more. Additionally, any number of phased-array antenna packages can be used, including more or less than the four phased-array circuit packages 501-504 shown in FIG. 5A.

In FIG. 5A, the antenna 500 is embodied as an "X" shaped array of antennas, although it is representative and other arrangements can be selected to give a preferred spatial coverage for aperture synthesis. For example, "Y" or "T"

shaped crosses can be used, as they provide good spatial coverage and angular resolution. As shown in the side view, no focusing lenses are needed for interferometric imaging, and the antenna 500 is relatively planar for imaging. Signals received on the antenna elements can be amplified and/or filtered by the amplifiers 114, and the phase shifters 116 can code multiplex each of the received signals, respectively, using unique codes generated by the modulators 118.

Figure 5B:
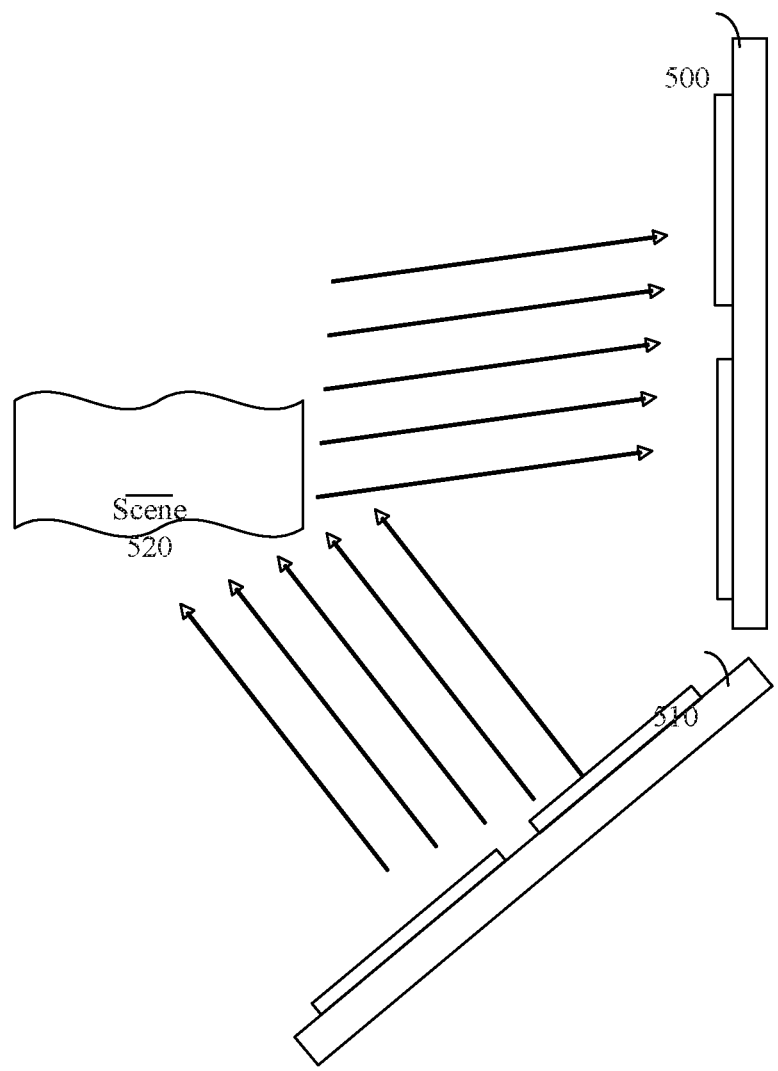
FIG. 5B illustrates an example illumination source for use with one or more of the interferometers in FIGS. 2-4, according to various embodiments described herein.

FIG. 5B illustrates an example illumination source 510 for use with one or more of the interferometers in FIGS. 2-4. In FIG. 5B, the illumination source 510 can be an active illumination source that generates and directs narrowband or broadband RF energy towards the scene 520. Because the interferometers described herein generate images based on the constructive and destructive interference of radiation that reflects off of objects, matter, etc., the illumination source 510 generates and directs radiation toward the scene 520 to illuminate it. As the radiation is reflected back from the scene 520, it can be captured by the antenna array 500 for processing.

The interferometers in FIGS. 2-4 can also operate as passive imagers which rely upon ambient illumination at mm-wave frequencies (e.g., from cold sky). This ambient radiation is blackbody in nature, with power levels proportional to the temperature of the source. Outdoors, cold sky approximately appears as a 100 degrees Kelvin (i.e., 100K) illumination source and people and surroundings appear as about 300K sources, providing a contrast ratio of about 200K. Indoors, the subject and surroundings are at similar temperatures and the contrast ratio is only around 10-15K. As such, sensitive receivers may be required to detect small temperature differences.

Active imaging includes illumination to elevate the signals above the noise floor. Illumination can be at a single frequency, similar to a radar, or over a wider range of frequencies, similar to a "white light" flashbulb. Illumination can be provided using commercial mm-wave transmitters to provide broadband illumination on the target. These can be modulated with pseudo-random gigabit-per-second codes to provide broadband "white" illumination. Additionally or alternatively, fluorescent light bulbs, including compact fluorescents and regular fluorescents, can be used to provide mm-wave illumination.

Figure 6:
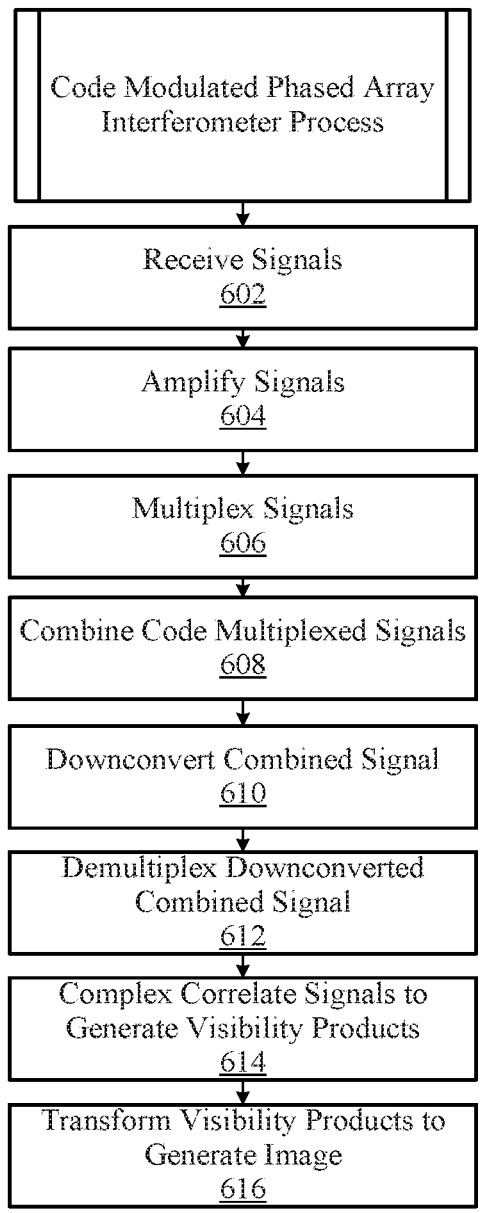
FIG. 6 illustrates an example code-modulated phased-array interferometer process according to various embodiments described herein.

FIG. 6 illustrates an example code-modulated phased-array interferometer process according to various embodiments described herein. The process is described below with reference to the interferometers 100A-100C in FIGS. 2-4, although variations on those types of interferometers and the components in those interferometers can be used to perform the process. Before turning to the process flow in FIG. 6, it is noted that the process may be practiced using an alternative order of the steps illustrated. That is, the process flow is provided as an example only, and the embodiments can be practiced using process flows that differ from that illustrated. For example, not all steps are required in every embodiment. One or more of the steps can be omitted or replaced, without departing from the spirit and scope of the embodiments. Further, steps may be performed in different orders, in parallel with one another, or omitted entirely, and/or certain additional steps may be performed.

At step 602, the process includes receiving a plurality of signals. For example, each of the antenna elements 112 shown in FIGS. 2-4 can be used to receive a respective one of the plurality of signals at step 602. At step 604, the process includes amplifying the plurality of signals received at step 602. The amplifiers 114 in FIGS. 2-4, which may be embodied as low noise or other suitable amplifiers, can be used for amplifying the signals. At step 606, the process includes multiplexing the plurality of signals (i.e., the amplified signals) to generate a plurality of code multiplexed signals. The phase shifters 116 in FIGS. 2-4 can be used to code multiplex each of the received signals, respectively, using unique codes generated by the modulators 118 at a suitable code or chip rate. The codes can be BOCPs as described herein. Further, the code or chip rate of the code-set can be selected based on a rate of scene changes in the image being captured.

At step 608, the process includes combining the plurality of code multiplexed signals into a combined signal. The combiner 120 in FIGS. 2-4 can be used to combine the plurality of code multiplexed signals as described above. At step 610, the process includes downconverting the combined signal to a downconverted combined signal, and the downconverter 130 in FIGS. 2-4 can be used for this step to downconvert the combined signal to a baseband or lower-frequency (e.g., intermediate frequency) combined signal. The downconverter 130 can also convert (e.g., analog to digital convert) the combined baseband signal for further processing in the digital domain.

At step 612, the process includes demultiplexing the downconverted combined signal into a plurality of baseband signals. As described above, the demultiplexing process can be considered a half-demultiplexing process. In various embodiments, the demultiplexing can be performed by the demultiplexers 142 shown in FIG. 3 or through a signal "squaring" operation similar to that performed by the squaring block 149 shown in FIG. 4.

At step 614, the process includes correlating unique pairs of the plurality of baseband signals to generate a plurality of visibility products. In various embodiments, the correlating can be performed by the complex correlator 144 shown in FIG. 3 or the correlators 148 shown in FIG. 4. At step 616, the process includes transforming the plurality of visibility products to generate an image, and this transforming can be performed by the Fourier Transformer 146 as described above and shown in FIGS. 2-4.

Figure 7:
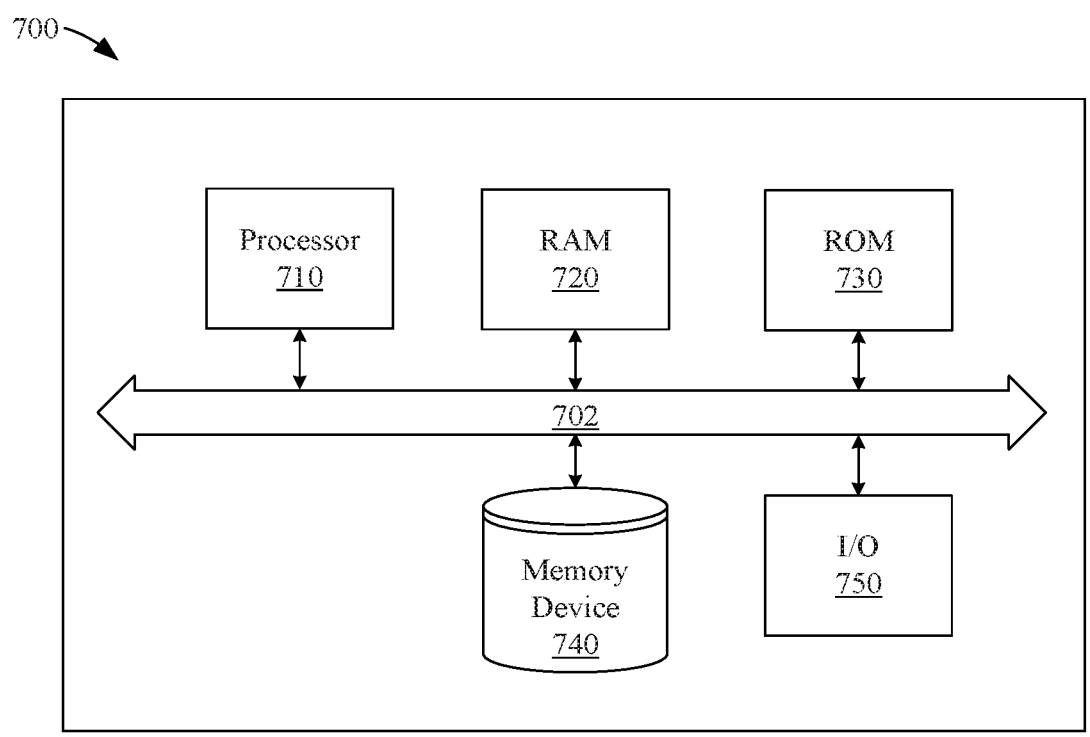
FIG. 7 illustrates an example schematic block diagram of a processing environment which may be relied upon, in part, in one or more of the interferometers in FIGS. 2-4, according to various embodiments described herein.

FIG. 7 illustrates an example schematic block diagram of a processing environment 700 which may be relied upon, in part, in one or more of the interferometers 100A-100C in FIGS. 2-4, according to various embodiments described herein. For example, the processing environment 700 may form part of the combiner 120, the downconverter 130, and/or image processor 140 in one or more of the interferometers 100A-100C. The processing environment 700 may be embodied, in part, using one or more elements of a mixed general and/or specific purpose computer. The processing environment 700 includes a processor 710, a Random Access Memory (RAM) 720, a Read Only Memory (ROM) 730, a memory device 740, and an Input Output (I/O) interface 750. The elements of processing environment 700 are communicatively coupled via one or more local interfaces 702. The elements of the processing environment 700 are not intended to be limiting in nature, as the architecture may omit elements or include additional or alternative elements.

In various embodiments, the processor 710 may be embodied as one or more circuits, general purpose processors, state machines, ASICs, or any combination thereof. In certain aspects and embodiments, the processor 710 is configured to execute one or more software modules which may be stored, for example, on the memory device 740. The software modules may configure the processor 710 to perform the tasks or operations undertaken by one or more of the interferometers 100A-100C in FIGS. 2-4.

The RAM and ROM 720 and 730 may include or be embodied as any random access and read only memory devices that store computer-readable instructions to be executed by the processor 710. The memory device 740 stores computer-readable instructions thereon that, when executed by the processor 710, direct the processor 710 to execute various aspects of the embodiments described herein.

As a non-limiting example group, the memory device 740 includes one or more non-transitory memory devices, such as an optical disc, a magnetic disc, a semiconductor memory (i.e., a semiconductor, floating gate, or similar flash based memory), a magnetic tape memory, a removable memory, combinations thereof, or any other known non-transitory memory device or means for storing computer-readable instructions. The I/O interface 750 includes device input and output interfaces, such as keyboard, pointing device, display, communication, and/or other interfaces. The one or more local interfaces 702 electrically and communicatively couples the processor 710, the RAM 720, the ROM 730, the memory device 740, and the I/O interface 750, so that data and instructions may be communicated among them.

In certain aspects, the processor 710 is configured to retrieve computer-readable instructions and data stored on the memory device 740, the RAM 720, the ROM 730, and/or other storage means, and copy the computer-readable instructions to the RAM 720 or the ROM 730 for execution, for example. The processor 710 is further configured to execute the computer-readable instructions to implement various aspects and features of the embodiments described herein. For example, the processor 710 may be adapted or configured to execute the demultiplexing and complex correlation operations described above. In embodiments where the processor 710 includes a state machine or ASIC, the processor 710 may include internal memory and registers for maintenance of data being processed.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

At least the following is claimed:

1. A code-modulated phased-array interferometer, comprising:
   a phased array comprising a plurality of receiver elements configured to receive a plurality of signals;
   a code multiplexer configured to multiplex the plurality of signals to generate a plurality of code multiplexed signals;
   a combiner configured to combine the plurality of code multiplexed signals into a combined signal; and
   a code demultiplexing image processor configured to:
      half-demultiplex a plurality of baseband signals from the combined signal;
      correlate unique pairs of the plurality of baseband signals to generate a plurality of visibility products; and
      Fourier transform the plurality of visibility products to generate an image.

2. The interferometer according to claim 1, further comprising a downconverter configured to downconvert the combined signal to a lower-frequency combined signal.

3. The interferometer according to claim 1, wherein the code multiplexer is configured to phase shift each of the plurality of signals according to a respective code to generate the plurality of code multiplexed signals.

4. The interferometer according to claim 1, wherein the code multiplexer is configured to phase shift each of the plurality of signals with a respective code from a code-set which has balanced orthogonal code products (BOCPs).

5. The interferometer according to claim 4, wherein the code-set has a chip rate selected based on a rate of scene changes in the image.

6. The interferometer according to claim 1, wherein the interferometer is configured to generate the image using ambient illumination.

7. The interferometer according to claim 1, further comprising:
   an active illumination source, wherein the interferometer generates the image using active illumination provided by the active illumination source.

8. The interferometer according to claim 7, wherein the active illumination source comprises at least one of a narrowband frequency transmitter or a broadband frequency transmitter.

9. The interferometer according to claim 7, wherein the active illumination source comprises a compact florescent illumination source.

10. A code modulated phased-array interferometer process, comprising:
    receiving, with a phased-array receiver, a plurality of signals;
    multiplexing, with the phased-array receiver, the plurality of signals to generate a plurality of code multiplexed signals;
    combining, with the phased-array receiver, the plurality of code multiplexed signals into a combined signal;
    half-demultiplexing, with a code demultiplexing image processor, a plurality of baseband signals from the combined signal;
    correlating, with the code demultiplexing image processor, unique pairs of the plurality of baseband signals to generate a plurality of visibility products; and
    transforming, with the code demultiplexing image processor, the plurality of visibility products to generate an image.

11. The process according to claim 10, wherein the multiplexing comprises multiplexing each of the plurality of signals according to a respective code to generate the plurality of code multiplexed signals.

12. The process according to claim 10, wherein the multiplexing comprises multiplexing each of the plurality of signals with a respective code from a code-set which has balanced orthogonal code products (BOCPs).

13. The process according to claim 12, wherein the code-set has a chip rate selected based on a rate of scene changes in the image.

14. The process according to claim 10, further comprising illuminating the image with an active illumination source.

15. The process according to claim 14, wherein the active illumination source includes at least one of a narrowband frequency transmitter or a broadband frequency transmitter.

16. A code-modulated phased-array interferometer, comprising:
    a phased array comprising a plurality of receiver elements configured to receive a plurality of signals;

a code multiplexer configured to multiplex the plurality of signals to generate a plurality of code multiplexed signals;

a combiner configured to combine the plurality of code multiplexed signals into a combined signal;

a downconverter configured to downconvert the combined signal to a lower-frequency combined signal; and a code demultiplexing image processor configured to:

half-demultiplex a plurality of baseband signals from the lower-frequency combined signal;

correlate unique pairs of the plurality of baseband signals to generate a plurality of visibility products; and Fourier transform the plurality of visibility products to generate an image.

17. The interferometer according to claim 16, wherein the code multiplexer is configured to phase shift each of the plurality of signals according to a respective code to generate the plurality of code multiplexed signals.

18. The interferometer according to claim 16, wherein the code multiplexer is configured to phase shift each of the plurality of signals with a respective code from a code-set which has balanced orthogonal code products (BOCPs).

19. The interferometer according to claim 18, wherein the code-set has a chip rate selected based on a rate of scene changes in the image.

20. The interferometer according to claim 16, wherein the interferometer generates the image using at least one of ambient illumination or active illumination provided by an active illumination source.

\* \* \* \* \*